United States Patent [19]

Chilton et al.

[11] Patent Number: 4,888,982
[45] Date of Patent: Dec. 26, 1989

[54] METHOD AND APPARATUS FOR EVALUATING THE HARDENING OF CHEMICALLY BONDED FOUNDRY SAND MOLDS AND CORES

[75] Inventors: David C. Chilton; Richard E. Simmons, both of Worcester, Great Britain

[73] Assignee: BCIRA, Birmingham, England

[21] Appl. No.: 241,619

[22] Filed: Sep. 8, 1988

[30] Foreign Application Priority Data

Sep. 8, 1987 [GB] United Kingdom ............... 8721043

[51] Int. Cl.$^4$ .............................................. G01N 3/48
[52] U.S. Cl. ........................................................ 73/81
[58] Field of Search .............................. 73/81, 82, 866

[56] References Cited

U.S. PATENT DOCUMENTS 2,509,692  5/1950  Miller ........................................ 73/81
4,059,990  11/1977  Glover et al. ............................ 73/81
4,331,026  5/1982  Howard et al. ......................... 73/81

FOREIGN PATENT DOCUMENTS 1951818  5/1970  Fed. Rep. of Germany ......... 73/81

Primary Examiner—Tom Noland
Assistant Examiner—Michele Simons
Attorney, Agent, or Firm—Scrivener and Clarke

[57] ABSTRACT

To ascertain when individual foundry molds and cores, bonded by a chemical method, have reached the requisition hardness, or still have the requisite hardness, a probe is pushed into the mold or core with a predetermined force, then withdrawn, and after a time interval it is pushed into a fresh point on the mold or core. This is repeated a number of times, each time in a different place, until the penetration is less than a predetermined value, indicating that the requisite hardness has been reached. Apparatus for doing this automatically can be portable and may signal by lamp and/or sound when the hardness has reached the required value. It may be modified to check whether the hardness of a core or mold made some time earlier has fallen below a given minimum value.

9 Claims, 1 Drawing Sheet

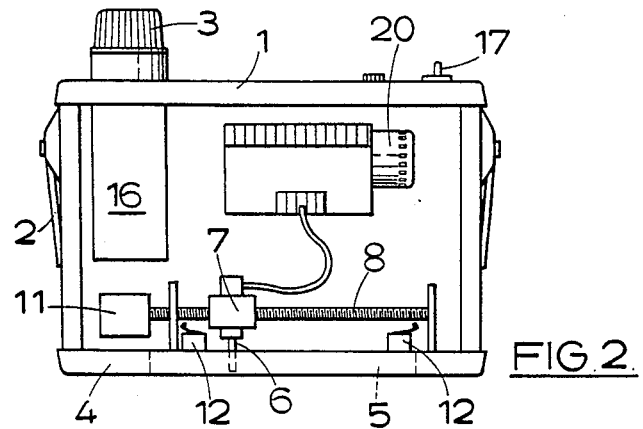
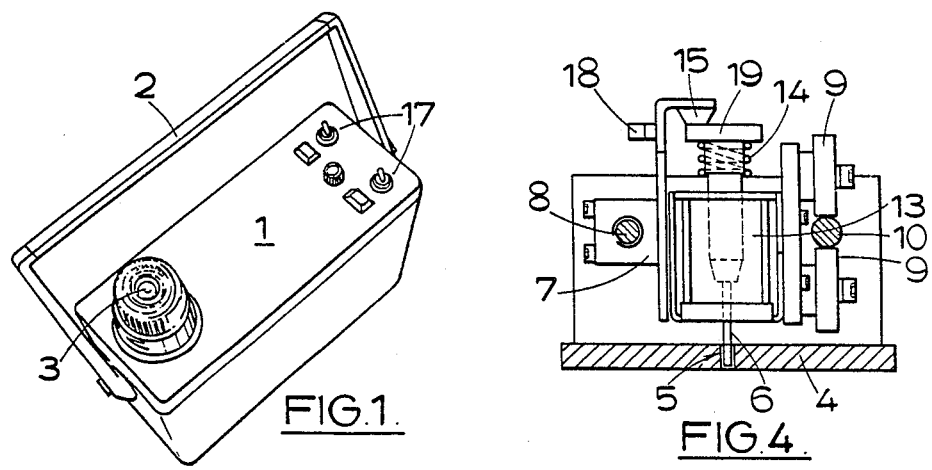
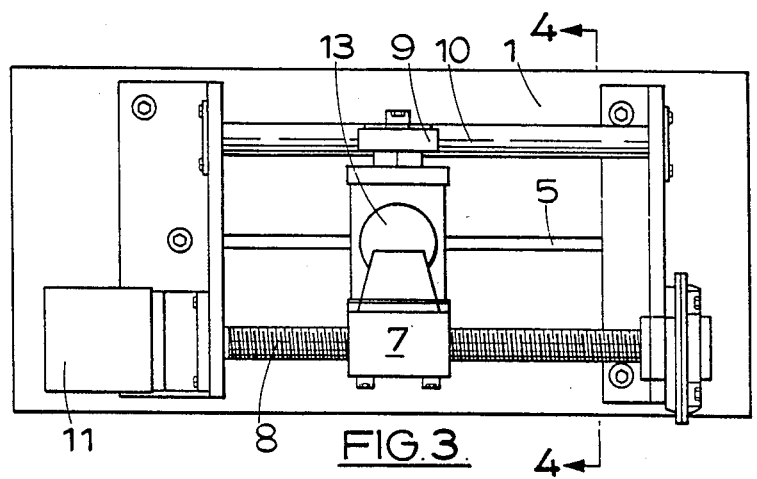

METHOD AND APPARATUS FOR EVALUATING THE HARDENING OF CHEMICALLY BONDED FOUNDRY SAND MOLDS AND CORES

This invention relates to a method and device which enables the development of the hardening of foundry moulds and cores made of chemically bonded refractory materials (referred to here for convenience as sand) to be monitored so that the foundryman can know as soon as possible when the core or mould is sufficiently hard to be stripped and handled. It may also be used to check the hardness of cores or moulds that have been in store for some time, to make sure that they have not become unacceptably soft.

Many castings are made in moulds constructed from sand grains bonded together with a chemical bonding material which confers upon the moulds considerable strength and rigidity necessary to produce sound castings. Some chemical bonding agents are hardened very rapidly by the application of a gas or a delayed reaction which takes place very rapidly after sufficient delay to allow the sand to be moulded around the pattern. Other chemical hardeners develop their strength only slowly after a period of time.

Chemical binders may be used either for making moulds or for making cores, but in either case it is necessary to pack the sand around a pattern in a box or to pack the sand into a shaped cavity in a box to produce a core. A core so produced must be removed from the box as soon as it is strong enough to sustain its own weight and dimensions. Occasionally the sand moulds are left in the box in which they were made, but they must be stripped from the pattern, and again this removal cannot be carried out until the sand has hardened sufficiently for the operation to be carried out without deformation of the mould. In the interests of economy it is desirable to have only one or a small number of each design of core box or moulding box and only one pattern, since these components are all expensive to produce and occupy storage space which is usually restricted. Therefore it is desirable that the sand should be removed from the pattern, the moulding box or the core box as soon as possible so that the boxes can be recycled for making the next mould or core.

The time taken by the sand to reach the necessary degree of hardening is not constant under all conditions. Many variables influence it, in particular the temperature of the sand, variations in the quality of the sand itself, whether or not the sand has been reclaimed after previous use, the amounts of chemical, catalyst or hardener used, and other atmospheric and operational variables. To allow for such variables it is usual to leave the sand to harden for a period of time so that it will always be strong enough to strip. This is wasteful of time since, on many occasions, hardening will have taken place some considerable time before stripping is carried out. This itself may be undesirable, since stripping becomes more difficult with time for some binder systems.

It is therefore desirable to have a way of ascertaining when the mould or core is strong enough to be removed from the box or the pattern without any change in dimensions during the stripping operation.

An important feature of many chemically bonded sands is that the hardening process takes place at different rates on the surface, which is exposed to the environment, and in the interior. It is therefore not acceptable merely to test the hardness of the exposed surface of the mould as a guide to its interior properties. Scratch tests and indentation tests which are used for baked cores or green sand moulds are therefore not suitable for the purpose envisaged. Neither can test pieces, made to represent the bulk of the sand, be acceptable as a reliable guide to stripping time. The most commonly used test method is the use of a penetration probe in which a long needle-shaped indentor with a sharp point is forced into the mould by a series of manually controlled impacts and the number of impacts to cause penetration to a certain predetermined depth measured. This method causes damage to moulds and cores and can split small cores, making them useless. The results can be very subjective as they can only be judged by the operator's observations and experience. Furthermore, to carry out the test requires an operator for the whole of the time of the tests and the results can only be judged by the operator's observations and experience.

The principal object of the present invention is to provide a convenient, non-subjective and non-destructive method of examining a mould or core after it has been made and of providing a signal as soon as the sand has hardened sufficiently for it to be removed from the pattern or box.

Another object is to provide apparatus for carrying out this method, preferably automatically and without the need for an operator in continuous attendance.

Another object is to provide a testing device which will be capable of testing cores or moulds which have been in store.

A major feature of the method and apparatus is the assurance that the chemical binder in the sand in the test area of the mould or core hardens at the same rate as that at the pattern or corebox face.

According to the invention there is proposed a method of evaluating the hardening of chemically bonded foundry sand moulds and cores comprising applying a given impulse to a probe to force the probe into a point on the surface of the mould or cores, withdrawing it, moving the probe to a fresh point and repeating the application of the force, this step being repeated a number of times while each time the penetration of the probe into the surface is monitored, and causing a signal to be given when the monitoring indicates that the penetration of the probe into the mould or core in one of the steps is less than a predetermined value, indicating that the requisite hardness is present.

The lateral movement of the probe between steps is preferably in a straight line. The steps can take place at timed intervals and the total time taken to reach the required hardness can be displayed.

In apparatus according to the invention for carrying out the method, the whole sequence may be automatic.

The apparatus may be fixed, but is preferably portable. In one version a housing has a base plate which is put in contact with the mould or core and this plate has in it a straight slot. Within the housing there is a traversing mechanism carrying the probe and its actuating means, and a timing and control device causes the probe to be projected through a given point near one end of the slot, then the probe is moved linearly a predetermined amount parallel to the slot, and the probe is caused to project again, this sequence being repeated until the detecting means indicate that the core or mould is hard enough.

The invention will now be further described by way of example with reference to the accompanying drawings, in which:

FIG. 1 is a perspective view of a portable version of the device;

FIG. 2 is a diagrammatic side view of the device with its interior exposed;

FIG. 3 is a plan view from above of the main mechanical parts of the device, including the base plate; and FIG. 4 is a simplified section through the parts shown in FIG. 3 on the line 4—4 in FIG. 3.

The device illustrated is designed to be portable and comprises a rectangular housing 1 with a handle 2 and a flashing xenon signal lamp 3 on its top face. It has a flat base plate 4 (FIG. 4) approximately 400 mm by 150 mm with a central slot 5 (FIG. 3) extending over the greater part of its length.

As will be described more fully later the device is placed on a flat portion of the mould or core under test with its base plate 4 in contact with the surface of the mould or core at least throughout the length of the slot 5. A blunt-ended needle-shaped probe 6 (FIG. 4) between 1.5 mm and 3 mm in diameter is mounted on a carriage 7 which is guided for movement on a lead screw 8, being located also by rollers 9 on the carriage engaging above and below a guide rail 10. The lead screw and rail are parallel with the slot 5 so that the carriage 7 can be displaced to move the probe 6 to any position along the length of the slot 5 under the control of an electric motor 11 driving the lead screw. The carriage is prevented from overrunning by limit switches 12, visible in FIG. 2 but not in FIG. 3, which terminate the test cycle and initiate an audible alarm 20 to indicate that the instrument should be reset to continue testing.

The probe 6 is vertically movable in relation to the carriage 7 and can be displaced downwards, to project through the slot 5 and into the body of sand on which the device is placed, by a pulse of current applied to a solenoid 13 surrounding the probe. The stroke may be of the order of 10 to 15 mm (into an unhardened mould or core). When the current ceases the probe is returned to its starting position by a spring 14, this position being determined by engagement with a fixed stop 15 on the carriage 7, and being such that the tip of the probe 6 is just flush with the lower face of the base plate.

The upper part of the housing 1 contains the electrical control equipment for traversing the carriage and actuating the probe in the manner described below. The control equipment includes a timing device 16, and externally accessible switches 17 for starting and stopping the operating sequence.

Where the device according to the invention is to be used in the preparation of a mould or core, then as soon as the sand has been placed in the moulding box or core box a metal, plastics or wooden plate of the same dimensions as the base plate 4 of the device is placed upon the surface of the sand and pressed flat. This provides a test surface isolated from the atmosphere until the device is ready to be placed upon the sand. The plate is then removed and replaced with the device. In this way the surface of the mould or core is protected from light, heat or air until the test device is applied, thereby ensuring that the surface area being tested is representative of conditions in the interior of the mould or core and especially at the pattern face.

With the carriage initially in its starting position holding the probe 6 at one end of the slot 5, the device is switched on. The solenoid is energised to cause the probe to penetrate the mould or core to a depth which, if the mould or core is still in a unhardened state, could be 10 or 15 mm. The probe is immediately withdrawn by the spring 14 and then after a predetermined time interval, which may conveniently be anything from a few seconds to 10 minutes, the motor 11 is energised to drive the lead screw 8 and move the carriage 7 a pre-set distance, for example, between 5 and 20 mm. The solenoid is then energised again, to cause the probe to penetrate the mould or core at a new position.

This cycle is repeated up to twenty or thirty times, the probe being gradually advanced along the slot 5, as long as the mould or core has not yet hardened to the required strength. The harder it becomes, the smaller is the penetration of the probe, and when the penetration falls below a predetermined amount, as detected by the shortened stroke, it is then known that the mould or core is hard enough to be stripped.

The size of the probe, the size of the solenoid and the strength of the spring are matched to the strength of the mould or core required at the hardening stage. This may be from 3.5 to $10.5 \times 10^5$ pascals equivalent compression strength.

The shortening of the stroke is detected by an optical sensor 18 which observes a head 19 on the probe and when that head fails to move below a predetermined horizontal plane, as detected by the sensor 18, when the solenoid is energised this indicates the required hardness has been reached. There is a time delay between energising the solenoid and the reading by the sensor to allow for the time taken by the probe to make its stroke.

In a typical case it is assumed that the required hardness has been reached when the stroke of the probe has fallen to 5 mm, and the optical sensor 18 is positioned accordingly. When the sensor shows that this condition has been reached it stops the cycle and initiates a signal which in the example shown is the illumination of the xenon lamp 3. Instead or in addition there could be a audible signal. At the same time the device may be re-set, i.e. the carriage is returned to its starting position.

In a modification a fixed time delay may be introduced between the response by the sensor 18 and the actuation of the signal. This provides a safety factor. For example the signal may be given only five or ten minutes after the minimum requisite hardness has been reached.

Where very long curing times may be present, the device can be arranged to be re-set, the alarm also being re-set.

The device may also be optionally fitted with a timer indicating the total time which has elapsed when the mould is ready to strip. The controls may also include indicators of the correct operation of the mechanism and of battery strength.

The device is portable and contains rechargeable electric batteries which energise the solenoid which operates the probe, the traversing mechanism of the probe from measuring point to measuring point, and the audible or visual warning device.

However, especially in highly automated foundries, it may be more convenient to have the device at a fixed point, and to bring the moulds or cores to it in succession. Also instead of the housing being stationary during the successive steps, it would be possible for the carriage to be omitted, and for the whole device to be advanced to move the probe from one point on the mould or core to another. Thus when we speak in the claims of moving the probe to a fresh point on the mould or core it will be understood that it would be possible within the scope of this phrase for the probe to be at a fixed point and for the mould or core to be advanced in steps past it.

Another possibility is for the device to be movable, but placed automatically on successive moulds or cores in turn.

The instrument may be left on one mould or core for the whole of its hardening up to the stripping time or, provided that the surfaces to be measured are kept covered by a plate before testing and when the instrument is removed, the instrument may be carried round and used successively on a number of different moulds or cores when it is thought that they are approaching their correct time for stripping. All that is necessary for each test is to re-set the instrument, remove the plate and place the instrument on the sand surface. After making a number of measurements it can then be removed and the plate replaced, after which it can be used to test other moulds or cores. Sometimes stripping times can be of the order of 1 or 2 hours, but in other cases times can be only a matter of parts of an hour, or minutes. The hardening rate will determine whether the instrument is to be left on a single mould or core until it has hardened sufficiently for stripping or moved from mould to mould or core to core for periodic checks while they are all hardening.

When long stripping times are encountered, especially in sands bonded with materials that can rapidly air-dry, it may be necessary on occasions to use a thin layer of plastics film, e.g. so-called cling-film, between the test area and the base plate of the instrument to eliminate air-drying effects at the slot 5 and ensure a successful test result.

Chemical binders for which this particular device is suitable are the self-setting materials such as furane or ester-silicate bonded moulds. However, any chemically bonded sand for which there is uncertainty about the stripping time can make use of the test instrument.

The features of the invention may be extended beyond those specially described above. The time at which sand has hardened sufficiently to strip is usually not sufficient for the sand to have hardened enough for casting. After stripping, the moulds or cores are usually allowed to stand for a further period of time before pouring takes place. While the strength of the sand to enable stripping to take place may be of the order of 3.5 to $10.5 \times 10^5$ pascals, for pouring to take place the mould may develop a strength of up to $35 \times 10^5$ pascals. An instrument using the same principle can be used for estimating the strength of the sand before pouring. Modifications would need to be made to adjust the method of loading the probe to provide sufficient energy to cause penetration of very hard moulds and well-established alternative mechanical devices for doing this can be employed. Similarily, an instrument of this kind could be employed for testing sand moulds and cores which have been stored for some considerable time and which may have softened with time to a stage where they are no longer suitable for making moulds. In this event the electrical controls would need to be adjusted so that the instrument would only give an indication of more penetration of the probe than a pre-set maximum takes place, indicating a soft mould.

We claim:

1. A portable apparatus for evaluating the hardening of chemically bonded foundry sand molds and cores comprising a housing designed to be placed in engagement with and to cover a surface of a foundry mold of core, said housing having a flat base plate protecting said covered surface from the atmosphere, said base plate including opening means therein, a probe including a solenoid mounted in said housing, energization of said solenoid applying a predetermined impulse to said probe to cause said probe to protect from said housing through said opening means in said base plate and penetrate the mold or core, means for subsequently withdrawing said probe and displacing said probe laterally in relation to said surface and said housing, said housing remaining in a fixed position relative to said mold or core, means for repeating the application of said impulse, subsequent withdrawal, and lateral displacement of said probe, and means for monitoring the stroke of said probe following each said impulse and giving a signal when the stroke is less than a predetermined value.

2. The apparatus set forth in claim 1 wherein said means for displacing said probe laterally comprise a carriage on which said probe is mounted within said housing and means for moving said carriage relative to said housing while said housing remains in a fixed position relative to the mold or core.

3. The apparatus set forth in claim 2 wherein said carriage moves linearly.

4. The apparatus set forth in claim 1 further including a timer serving to initiate the lateral displacement of said probe sat regular intervals.

5. The apparatus set forth in claim 1 wherein said monitoring means comprise an optical sensor sensing the position of said probe a predetermined time after application of said impulse.

6. A method of evaluating the hardening of chemically bonded foundry sand molds and cores utilizing apparatus according to claim 1 said method comprising the steps of applying a given impulse to said probe to force said probe into a point on the surface of said mold or core, withdrawing said probe, moving said probe to a fresh point and reapplying said impulse to said probe to force said probe into another point on the surface of said mold or core, repeating said steps a number of times, monitoring each penetration of said probe into said surface, and causing a signal to be given when said monitoring indicates that a penetration of said probe into said mold or core is less than a predetermined value, indicating that the requisite hardness is present 7. The method set forth in claim 6 wherein said points are in a straight line.

8. The method set forth in claim 6 wherein said impulse is applied by an electric solenoid.

9. The method set forth in claim 6 wherein the successive steps are performed automatically at timed intervals.

* * * * *